United States Patent [19]
Glastra

[11] Patent Number: 5,632,763
[45] Date of Patent: May 27, 1997

[54] BIFURCATED STENT AND METHOD FOR IMPLANTING SAME

[75] Inventor: Hendrik Glastra, Enschede, Netherlands

[73] Assignee: Cordis Corporation, Miami Lakes, Fla.

[21] Appl. No.: 588,513

[22] Filed: Jan. 18, 1996

[30] Foreign Application Priority Data

Jan. 19, 1995 [NL] Netherlands ............... 9500094

[51] Int. Cl.⁶ ................................. A61M 29/00
[52] U.S. Cl. ................. 606/194; 606/198; 623/1; 623/12
[58] Field of Search ............... 606/191, 192, 606/194, 197, 198, 195; 604/1, 12

[56] References Cited

U.S. PATENT DOCUMENTS

| | | |
|---|---|---|
| 4,872,874 | 10/1989 | Taheri . |
| 4,994,071 | 2/1991 | MacGregor ............... 606/194 |
| 5,219,355 | 6/1993 | Parodi et al. ............ 606/191 |
| 5,316,023 | 5/1994 | Palmaz et al. ........... 606/198 |
| 5,342,300 | 8/1994 | Stefanadis et al. . |

FOREIGN PATENT DOCUMENTS

| | | |
|---|---|---|
| 0521573 | 1/1993 | European Pat. Off. . |
| 0551179 | 7/1993 | European Pat. Off. . |
| 0617930 | 10/1994 | European Pat. Off. . |

*Primary Examiner*—Michael Buiz
*Assistant Examiner*—Kevin Truong
*Attorney, Agent, or Firm*—Lockwood, Alex, Fitzgibbon & Cummings

[57] ABSTRACT

A stent particularly useful in reinforcing bifurcated arteries includes a first primary stent arranged inside a major artery, such the aorta at the level of the bifurcation and at least two secondary cylindrical stents. Each secondary stent is placed inside of a branching artery and inside the lumen of the first primary stent. The secondary stents engage interior portions of the primary stent and are anchored thereto by expansion.

23 Claims, 3 Drawing Sheets

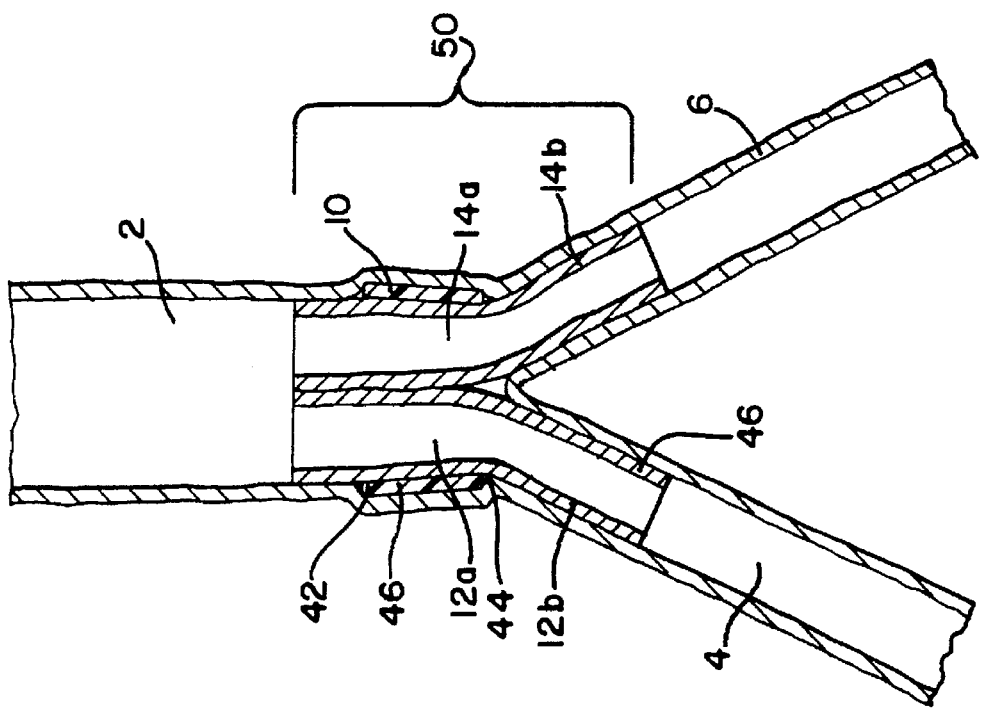
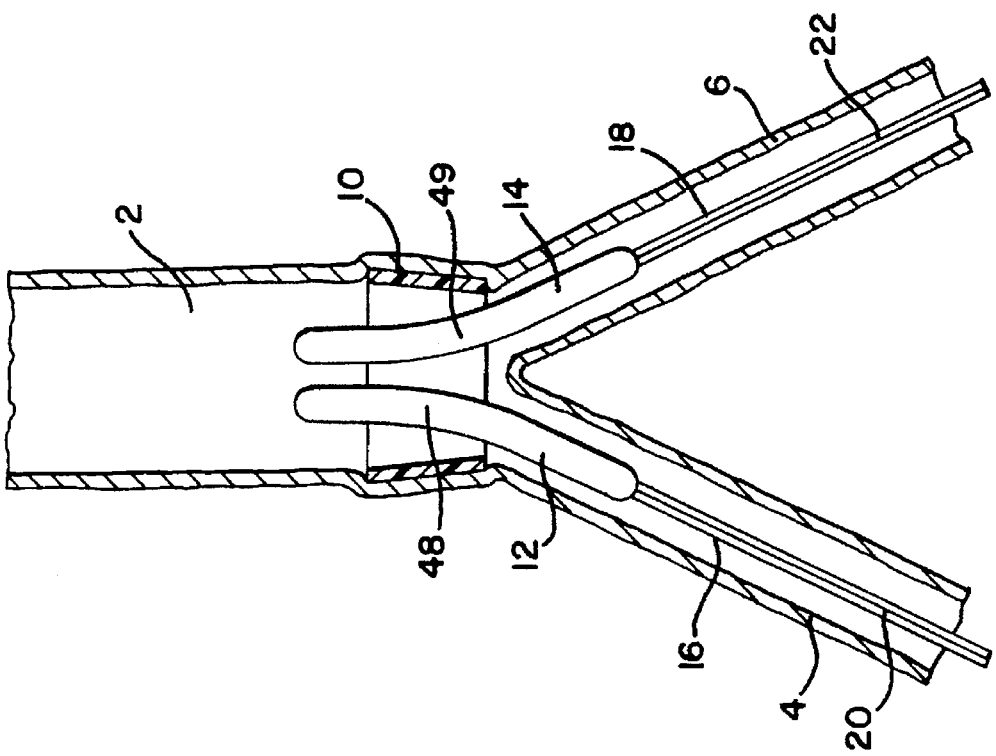

BIFURCATED STENT AND METHOD FOR IMPLANTING SAME

BACKGROUND AND SUMMARY OF THE INVENTION

The present invention relates generally to stents, and more particularly to an implantable bifurcated stent used to reinforce the bifurcation of the aorta into arteries leading to the lower limbs and a method for positioning such a stent within a blood vessel.

Stents are commonly used to repair compromised blood vessels in the body. Such stents may be used to repair compromised coronary arteries which have become narrowed or altogether blocked by the build up of plaque. They may also be used to replace compromised blood vessels, such as the aorta, which have developed enlarged, weakened areas known as aneurysms. In the aorta, aneurysms may often occur in the areas where the aorta divides into two secondary arteries, such as the two common iliac arteries, which supply blood to the lower limbs.

Previously, such aneurysms were repaired by surgery by making an incision in the patient's body and cutting into the aorta and implanting a tubular graft into the artery to replace the portion of the artery compromised by the aneurysm.

This surgery poses a problem where the aneurysm occurs at locations where one blood vessel branches off into two subsidiary blood vessels. One solution for arterial repairs at such a location has been proposed in European Patent Application EP-A-0 551 179, published Jul. 14, 1993 wherein two separate bypass grafts are introduced into an aortic branch. These two grafts are intraluminally delivered through the artery to the aneurysm and secured therein by means of two dilation catheters. This structure relies solely upon the expansion of the bilateral grafts against each other within the aorta and therefore requires very accurate sizing of the grafts and placement in the aorta. This structure may be problematic in that the aortic ends of the grafts may work themselves free under arterial pressure.

It is therefore desirable to develop a graft, or stent, for use in bifurcated blood vessels which is self-supporting and may be advantageously used to reinforce bifurcated portions of the aorta as well as other blood vessels.

Such a stent can be employed in an advantageous manner to reinforce the bifurcation of the aorta or another artery into the two smaller arteries leading to the lower limbs. With the present state of technology such a stent is not available and in the case of a lesion on the artery, it is often necessary to replace the entire section of the artery by a new, artificial blood vessel section (a bifurcation prosthesis). The surgery involved in such a procedure usually lasts several hours, entails a high degree of risk and is a great burden to the patient.

The present invention is therefore directed to a stent which makes the above described surgeries superfluous and is characterized by a first, or primary, stent placed inside an artery at the level of the bifurcation and at least two cylindrical secondary stents, each of which is partially placed within the arterial sections branching off of the artery, and with the remaining sections of the secondary stent being placed inside the lumen of the first stent.

In its preferred embodiment the present invention provides a bifurcated stent assembly having a Y-shaped configuration. The Y-shaped stent includes, as mentioned above, a base or primary stent which is fixed securely in the artery near to the location at which it divides into two branch arteries. The secondary stents are positioned both inside this first stent and inside the branching arteries and are fixed in a reliable and sealing manner to the first stent at one end and to the branching artery on the other end.

In particular, when stents are used which are disclosed in applicant's European patent application EP-A0 521 573 and EP-A-0 617 930 in forming the bifurcated stent assembly, a reliable and sealed anchoring within the bifurcated blood vessels is obtained as a result of the specific configuration of this stent.

Accordingly, it is a general object of the present invention to provide a bifurcated stent for intraluminal delivery to a bifurcated artery affected by lesions.

It is another object of the present invention to provide a bifurcated stent assembly for intraluminal delivery comprising a first primary stent having a partially conical shape and at least two secondary stents, each having a cylindrical configuration, the primary stent being intraluminally delivered to the arterial bifurcation and providing a base, or support, for the secondary stents.

It is still another object of the present invention to provide a bifurcated stent having a base portion which is placed within an artery upstream of and proximate to the affected area of the artery, the base portion providing an anchoring surface within the artery, and a number of secondary cylindrical stents which are intraluminally delivered to the affected arterial area and which extend through the base portion into the bifurcated arteries, the upstream ends of the secondary stents being anchored to the arteries by being joined to the base portion while the downstream, distal ends of the secondary stents extend into the branch arteries.

It is still a further object of the present invention to provide a method of repairing or reinforcing bifurcated blood vessels by first delivering and attaching an anchoring stent to an artery and subsequently delivering and attaching secondary stents to the anchoring stent and to the bifurcations of the artery.

These and other objects, features and advantages of the present invention will be clearly understood through a consideration of the following detailed description.

BRIEF DESCRIPTION OF THE DRAWINGS

In the course of the following detailed description, reference will be frequently made to the accompanying drawings in which:

FIG. 3 is the same view of FIG. 2, illustrating the placement by way of two dilation catheters of two secondary stents within the bifurcations of the artery;

FIG. 4 is the same view as FIG. 2 illustrating a completed bifurcated stent formed in the artery and its bifurcations after expansion and curing of the secondary stents;

DETAILED DESCRIPTION OF THE PREFERRED EMBODIMENT

Figure 2:
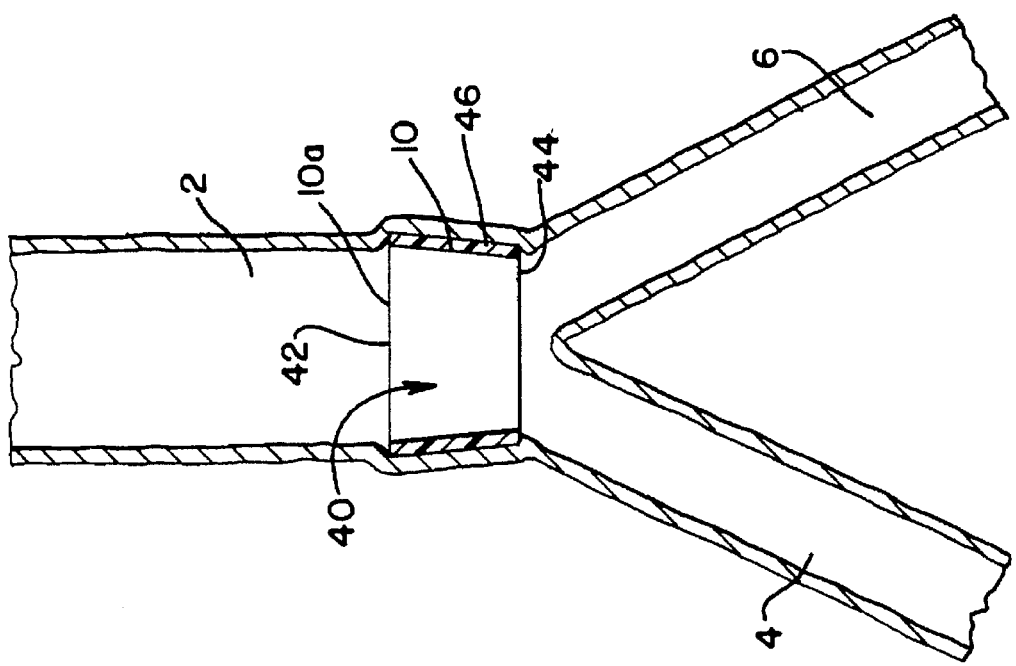
FIG. 2 is the same view as FIG. 1, but illustrating the placement of a first base stent within the body portions of the artery.
Figure 1:
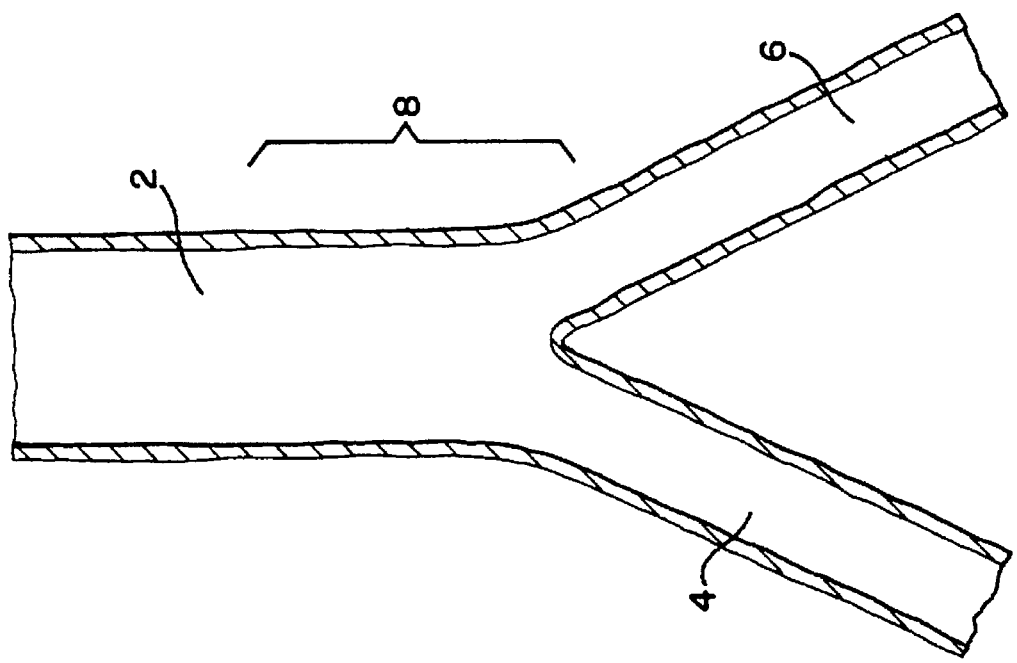
FIG. 1 is a schematic sectional view illustrating a bifurcated artery exemplary of the environment in which the present invention is employed.

FIG. 1 illustrates schematically and in a longitudinal cross-section a bifurcated blood vessel, such as the aorta 2 and two smaller arteries 4, 6 branching off therefrom. For the most part, the branch arteries lead to body extremities or to the respective lower limbs. The region of the bifurcation, in particular the area indicated by the bracket 8 in FIG. 1, is compromised and in need of repair. Such a compromise may have been affected by either an impairment or weakening of the wall of the blood vessel or the lumen of the vessel(s) are occluded to a greater or lesser degree. So far, such a lesion could only be cured by replacing both the bifurcation and a section of the artery with artificial blood vessels, such as a bifurcation prosthesis, involving major surgery and a high degree of risk.

With the stent and the method according to the invention respectively, such an operation has become superfluous.

In accordance with the present invention, a first or base stent 10 is placed inside the aorta 2. The base stent 10 is illustrated in the Figures as having a generally conical configuration with a like cone-shaped lumen 40 extending therethrough. Other shapes may also be used for the base stent 10, such as a cylindrical base portion with a cone-shaped lumen or a cylindrical lumen. The lumen 40 has two opposing ends 42 and 44 with one end 42 having a diameter which is generally greater than the other end 44. This lumen opening 42 is generally even with the upstream end 10a of the stent 10. The end 42 of the greater diameter may be referred to as the "upstream" end of the lumen 40 with respect to its location in the artery 2 relative to the flow of blood through the artery 2 inasmuch as the blood flows through end 42 first and then exits from the opposing, downstream end 44.

The stent 10 is preferably of the type described in EP-A-0 521 573 and EP-A-0 617 930 and is positioned by means of the method described in these publications, whereby the lumen 40 with the largest diameter is directed away, at 42, from the bifurcated arteries 4 and 6.

Figure 5:
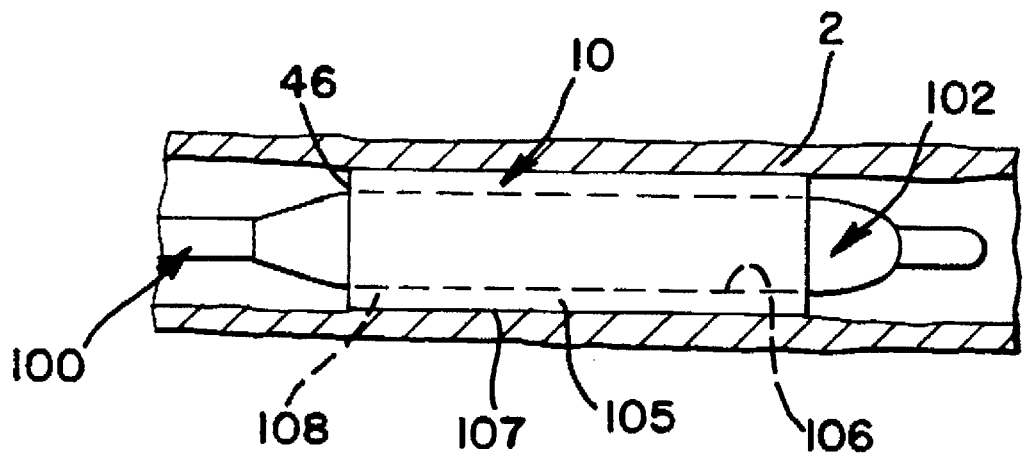
FIG. 5 is a longitudinal view, partially in section, of a stent-balloon catheter assembly inside of a blood vessel.
Figure 6:
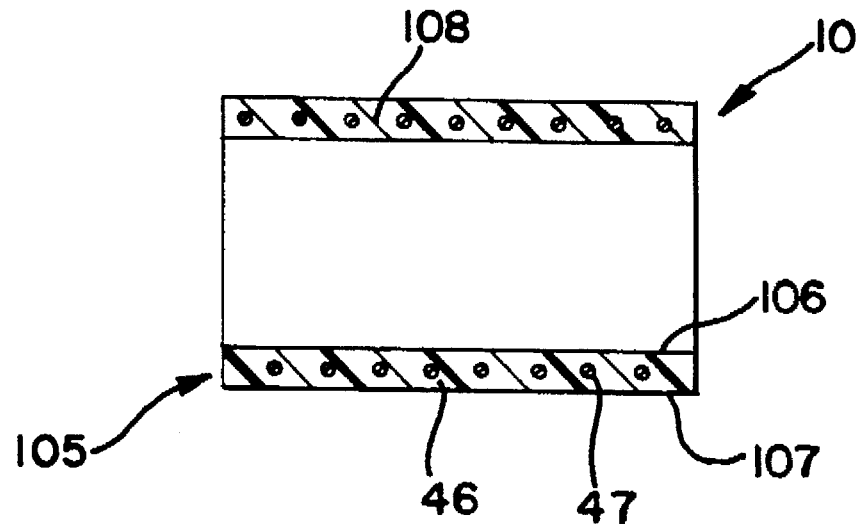
FIG. 6 is a sectional view of a stent utilized in the present invention.

As described in the aforementioned publications, which are incorporated herein by reference, and as described in the exemplary drawings of FIGS. 5 and 6, such a stent 10 may be placed into the blood vessel by inserting a catheter 100 having an inflatable balloon 102 disposed at its distal end into the blood vessel 2 and positioning it at the compromised area 8, whether it be a narrowing or an aneurysm. A stent 10 is placed over the balloon 102 prior to insertion and may be particularly sized to fit the blood vessel. In this regard, the diameter of the stent 10, when expanded, into its final state may range from about 2.5 mm when used in a cardiac application to about up to 20 mm or even more when used to reinforce the wall of a major artery, such as the aorta, in the case of an aneurysm.

As mentioned in greater detail below, the stent includes a radiation-curable material 46, such as an acrylate, which is curable by light radiation such as laser light or ultraviolet light. The stent 10, as explained in the publication EP-A-0 617 930 referenced above may include an inner absorbent material having a mesh-like or other suitable configuration. The open portions, or cells of the absorbent material retain the curable material 104 in place.

The stent may be formed in the configuration of a sleeve 105 having inner and outer walls 106, 107 which define an annular space 108 therebetween which may be filled with either the curable material 46 alone or an absorbent material 47 impregnated with the curable material 46 as illustrated in FIG. 6. This sleeve 105 is fitted over the inflation balloon 102 and may be folded or spirally wrapped around it as is known in the art and then inserted into the blood vessel for positioning and in placement at the compromised section thereof. When the balloon 102 is inflated, the stent is pressed against the blood vessel or expanded to its maximum diameter(s). Once inflated, radiation in the form of laser light or ultraviolet light may be emitted from a fiber-optic cable (not shown) onto the curable material 104 in order to cause it to set in place.

After the base stent 10 is placed in the blood vessel, a cylindrical stent assembly, indicated in FIG. 3 as cylindrical stents 12 and 14 respectively, is placed, via the branching arteries 4, 6 inside the stent 10. This secondary stent assembly may be moved into place through the bifurcated arteries 4, 6 until, as illustrated, the secondary stents 12, 14 extend from the branching sections 4, 6 into the artery 2 through the base stent 10.

The secondary stent assembly utilizes two expandable carrier balloons 48, 49 connected to accessory catheters 16, 18 respectively. Arranged around the balloons are sleeve-shaped cylindrical secondary stents 12 and 14 which expand on expansion of the carrier balloon. By irradiating the curable material inside the expandable sleeve by means of suitable radiation (e.g. ultraviolet radiation), supplied via internal optic fibers 20, 22 respectively, the material will cure to form the completed stent assembly 50 in place within the bifurcated portion of the artery 2. This assembly 50 will remain firmly anchored in position after withdrawal of the deflated carrier balloons. The secondary stents 12, 14 may have the same length and as illustrated, they may be aligned such that their upstream end portions 50 extent past the upstream opening 42 of the base stent lumen 40. Similarly, these secondary stent upstream end portions 50 may be aligned together to prevent flow disruptions from occurring.

The base stent 10 which is fixed inside of the aorta 2 receives the upper sections 12a, 14a of the two cylindrical stents 12, 14 while the lower sections 12b, 14b thereof are fixed inside of the branching arteries 4, 6 due to this expansion and curing. As a result, they adapt perfectly to the shape of the blood vessels and lumen of the first stent 10 respectively and it is ensured that both stents make a close, sealing contact with the inner wall of the aorta 2, the inner wall of the stent 10 and the inner walls of the arteries 4, 6 respectively. In effect the secondary stents 12, 14 occupy substantially all of the interior of the base stent lumen 40. In order to strengthen the contact between the base and secondary stents, either of them may include an adhesive coating suitable for body use.

While the preferred embodiment of the invention has been shown and described, it will be understood by those skilled in the art the changes or modifications may be made thereto without departing from the true spirit and scope of the invention.

I claim:

1. A bifurcated stent assembly useful for repairing a compromised section of a bifurcated blood vessel, the compromised section of the blood vessel occurring near the bifurcation, said bifurcation including at least two subsidiary blood vessels branching off from said blood vessel, the stent assembly comprising: a primary stent adapted to engage said blood vessel proximate to said bifurcation and at least two secondary stents adapted to engage respective ones of said at least two subsidiary blood vessels, each of the secondary stents having a length sufficient to extend from its respective subsidiary blood vessel into said primary stent and into engagement with at least a portion of an interior surface of said primary stent whereby said secondary stents are held in place within said bifurcation.

2. The stent assembly as claimed in claim 1, wherein said primary stent is generally conical in configuration and has two opposing ends, a first of said two ends being disposed generally adjacent said subsidiary blood vessels and a second of said two ends being disposed generally away from said subsidiary blood vessels, said primary stent second end having a diameter which greater than that of said primary stent first end.

3. The stent assembly as claimed in claim 1, wherein said secondary stents are generally cylindrical.

4. The stent assembly as claimed in claim 2, wherein said secondary stents are generally cylindrical.

5. The stent assembly as claimed in claim 2, wherein said secondary stents have portions which project past said primary stent second end.

6. The stent assembly as claimed in claim 1, wherein at least one of said primary and secondary stents is formed from a radiation-curable material.

7. The stent assembly as claimed in claim 1, wherein said primary and secondary stents are formed from radiation-curable materials.

8. The stent assembly as claimed in claim 6, wherein said radiation-curable material is an acrylate.

9. The stent assembly as claimed in claim 1, wherein at least one of said primary and secondary stents includes a sleeve of radiation-curable material.

10. The stent assembly as claimed in claim 1, wherein said secondary stents are expanded into place against said primary stent interior surface.

11. The stent assembly as claimed in claim 1, wherein said primary stent has a generally conical lumen.

12. An implantable stent for repairing a compromised section of a bifurcated section of a blood vessel, the bifurcated blood vessel section including a primary blood vessel and at least two secondary blood vessels meeting at and branching off from the primary blood vessel, the stent comprising a hollow base portion having a generally conical configuration and adapted to be expanded into place within said primary blood vessel, the base portion having opposing first and second openings communicating with an internal passage of said base portion, said base portion first opening facing away from said secondary blood vessels and said base portion second opening facing said secondary blood vessels, said stent further including at least two elongated, hollow secondary portions having generally cylindrical configurations, each of the secondary portions having respective first and second openings disposed at opposing first and second ends thereof which communicate with respective internal passages of secondary portions, said secondary portions extending through said base portion, said secondary portions having generally common lengths such that said second ends thereof extend into said secondary blood vessels and said first ends pass through said base portion, outer surfaces of said secondary portions near said first ends thereof engaging parts of said base portion internal passage.

13. The stent as claimed in claim 12, wherein said base portion internal passage is generally conical and said base portion first opening is larger than said base portion second opening.

14. The stent as claimed in claim 12, wherein said two secondary portions have substantially the same length.

15. The stent as claimed in claim 12, wherein said base and secondary portions are formed from a radiation-curable material.

16. The stent as claimed in claim 15, wherein said radiation-curable material is an acrylate.

17. The stent as claimed in claim 12, wherein said secondary portion first ends project past said base portion first opening.

18. The stent as claimed in claim 12, wherein said secondary portions are expanded against each other and said base portion within said base portion to occupy substantially all of said base portion internal passage.

19. A method for forming a bifurcated stent within a bifurcated area of a blood vessel wherein the bifurcated area includes a primary blood vessel portion and at least two secondary blood vessel portions branching off from said primary blood vessel portion, the method comprising the following steps:

positioning a first stent having a interior lumen within said primary blood vessel portion by expanding the first stent against said primary blood vessel portion;

positioning a secondary stent in each of the secondary blood vessel portions branching off of said primary blood vessel portion such that first portions of said secondary stents at least partially extend into said first stent lumen and second portions of said secondary stents respectively extend into said secondary blood vessel portions; and fixing said secondary stents in place within said first stent lumen and said secondary blood vessel portions.

20. The method according to claim 19, wherein said positioning steps are accomplished by placing such first and secondary stents into inflatable balloon portions of balloon catheters and inflating said balloon portions to expand said first and secondary stents into place within said primary and secondary blood vessel portions.

21. The method according to claim 19, further including the step of positioning said secondary stents within said first stent lumen such that common opposing ends of said secondary stents project past opposing ends of said first stent.

22. The method according to claim 19, wherein said first stent lumen is conical in shape and said first stent is positioned in said primary blood vessel portion such that the largest opening of said lumen is directed away from the secondary blood vessel portions.

23. The method according to claim 19, wherein said first and secondary stents include a radiation-curable material and said method further includes the step of exposing said first and secondary stents to radiation to cure said radiation curable material after said first and secondary stents are positioned in place.

* * * * *